(12) United States Patent
Linares

(10) Patent No.: US 6,510,559 B1
(45) Date of Patent: Jan. 28, 2003

(54) PROTECTIVE TORSO GARMENT

(76) Inventor: Lazaro V. Linares, 410 NW. 106th St., Miami, FL (US) 33150

( * ) Notice: Subject to any disclaimer, the term of this patent is extended or adjusted under 35 U.S.C. 154(b) by 0 days.

(21) Appl. No.: 09/653,909

(22) Filed: Sep. 1, 2000

(51) Int. Cl.[7] ................................. A41D 1/00
(52) U.S. Cl. ................................. 2/96; 2/462
(58) Field of Search ............... 2/462, 463, 461, 2/465, 69, 76, 108, 102, 115, 2.5, 96, 237, 80, 44, 83, 45, 85, 269, 121, 104, 105, 106, 114, 270, 265–266

(56) References Cited

U.S. PATENT DOCUMENTS

| | | | |
|---|---|---|---|
| 1,010,679 A | * 12/1911 | Padernacht | 2/105 Q |
| D162,953 S | 4/1951 | Haywoard | |
| 3,064,265 A | * 11/1962 | Bridgewaters | 2/74 |
| 3,094,703 A | * 6/1963 | Bailey | 2/96 |
| 3,793,645 A | * 2/1974 | Kadison | 2/221 |
| 4,677,699 A | 7/1987 | Barabe | |
| 4,683,595 A | * 8/1987 | Cash | 2/105 |
| 4,821,343 A | 4/1989 | Quealy | |
| 5,008,959 A | 4/1991 | Coppage, Jr. et al. | |
| 5,144,694 A | * 9/1992 | Conrad Daould et al. | 2/69 |
| 5,338,290 A | 8/1994 | Aboud | |
| 5,343,564 A | 9/1994 | Reynolds et al. | |
| 5,373,582 A | * 12/1994 | Dragone et al. | 2/2.5 |
| 5,465,424 A | * 11/1995 | Cudney et al. | 2/456 |
| 5,495,621 A | * 3/1996 | Kibbee | 2/2.5 |
| 5,548,843 A | * 8/1996 | Chase et al. | 2/102 |
| 5,669,077 A | * 9/1997 | Stewart | 2/227 |
| 5,692,238 A | * 12/1997 | Watson | 2/102 |
| 5,754,982 A | * 5/1998 | Gainer | 2/2.5 |
| 5,873,768 A | * 2/1999 | Fleischmann-Ament et al. | 2/73 |
| 6,014,772 A | * 1/2000 | Connelly | 2/69 |
| 6,048,253 A | * 4/2000 | Larsen | 2/44 |
| 6,209,135 B1 | * 4/2001 | Irvin | 2/102 |

* cited by examiner

*Primary Examiner*—John J. Calvert
*Assistant Examiner*—Tejash Patel

(57) ABSTRACT

A protective torso garment for providing support and pressure against an injured rib cage. The protective torso garment includes a panel. The panel has a outer surface, a inner surface, a first side edge, a second side edge, a top edge and a bottom edge. The panel comprises a resiliently elastic cloth material. Each of a pair of shoulder straps has a first end and a second end. Each of the ends the shoulder straps is securely attached to the top edge of the panel. The second ends are generally positioned between first and second side edges. Each of the first ends of the straps is positioned respectively adjacent to one of the side edges of the panel. A securing means detachably attaches the first side edge to the second side edge.

2 Claims, 2 Drawing Sheets

PROTECTIVE TORSO GARMENT

BACKGROUND OF THE INVENTION

1. Field of the Invention

The present invention relates to protective garments and more particularly pertains to a new protective torso garment for providing support and pressure against an injured rib cage.

2. Description of the Prior Art

The use of protective garments is known in the prior art. More specifically, protective garments heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,338,290; 4,677,699; 4,821,343; 5,343,564; 5,008,959; and U.S. Des. Pat. No. 162,953.

While these devices fulfill their respective, particular objectives and requirements, the aforementioned patents do not disclose a new protective torso garment. The inventive device includes a panel. The panel has a outer surface, a inner surface, a first side edge, a second side edge, a top edge and a bottom edge. The panel comprises a resiliently elastic cloth material. Each of a pair of shoulder straps has a first end and a second end. Each of the ends the shoulder straps is securely attached to the top edge of the panel. The second ends are generally positioned between first and second side edges. Each of the first ends of the straps is positioned respectively adjacent to one of the side edges of the panel. A securing means detachably attaches the first side edge to the second side edge.

In these respects, the protective torso garment according to the present invention substantially departs from the conventional concepts and designs of the prior art, and in so doing provides an apparatus primarily developed for the purpose of providing support and pressure against an injured rib cage.

SUMMARY OF THE INVENTION

In view of the foregoing disadvantages inherent in the known types of protective garments now present in the prior art, the present invention provides a new protective torso garment construction wherein the same can be utilized for providing support and pressure against an injured rib cage.

The general purpose of the present invention, which will be described subsequently in greater detail, is to provide a new protective torso garment apparatus and method which has many of the advantages of the protective garments mentioned heretofore and many novel features that result in a new protective torso garment which is not anticipated, rendered obvious, suggested, or even implied by any of the prior art protective garments, either alone or in any combination thereof.

To attain this, the present invention generally comprises a panel. The panel has a outer surface, a inner surface, a first side edge, a second side edge, a top edge and a bottom edge. The panel comprises a resiliently elastic cloth material. Each of a pair of shoulder straps has a first end and a second end. Each of the ends the shoulder straps is securely attached to the top edge of the panel. The second ends are generally positioned between first and second side edges. Each of the first ends of the straps is positioned respectively adjacent to one of the side edges of the panel. A securing means detachably attaches the first side edge to the second side edge.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new protective torso garment apparatus and method which has many of the advantages of the protective garments mentioned heretofore and many novel features that result in a new protective torso garment which is not anticipated, rendered obvious, suggested, or even implied by any of the prior art protective garments, either alone or in any combination thereof.

It is another object of the present invention to provide a new protective torso garment which may be easily and efficiently manufactured and marketed.

It is a further object of the present invention to provide a new protective torso garment which is of a durable and reliable construction.

An even further object of the present invention is to provide a new protective torso garment which is susceptible of a low cost of manufacture with regard to both materials and labor, and which accordingly is then susceptible of low prices of sale to the consuming public, thereby making such protective torso garment economically available to the buying public.

Still yet another object of the present invention is to provide a new protective torso garment which provides in the apparatuses and methods of the prior art some of the advantages thereof, while simultaneously overcoming some of the disadvantages normally associated therewith.

Still another object of the present invention is to provide a new protective torso garment for providing support and pressure against an injured rib cage.

Yet another object of the present invention is to provide a new protective torso garment which includes a panel. The panel has a outer surface, a inner surface, a first side edge, a second side edge, a top edge and a bottom edge. The panel comprises a resiliently elastic cloth material. Each of a pair of shoulder straps has a first end and a second end. Each of the ends the shoulder straps is securely attached to the top edge of the panel. The second ends are generally positioned between first and second side edges. Each of the first ends of the straps is positioned respectively adjacent to one of the side edges of the panel. A securing means detachably attaches the first side edge to the second side edge.

Still yet another object of the present invention is to provide a new protective torso garment that is easily taken on and off for a person who would otherwise be in pain while dressing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
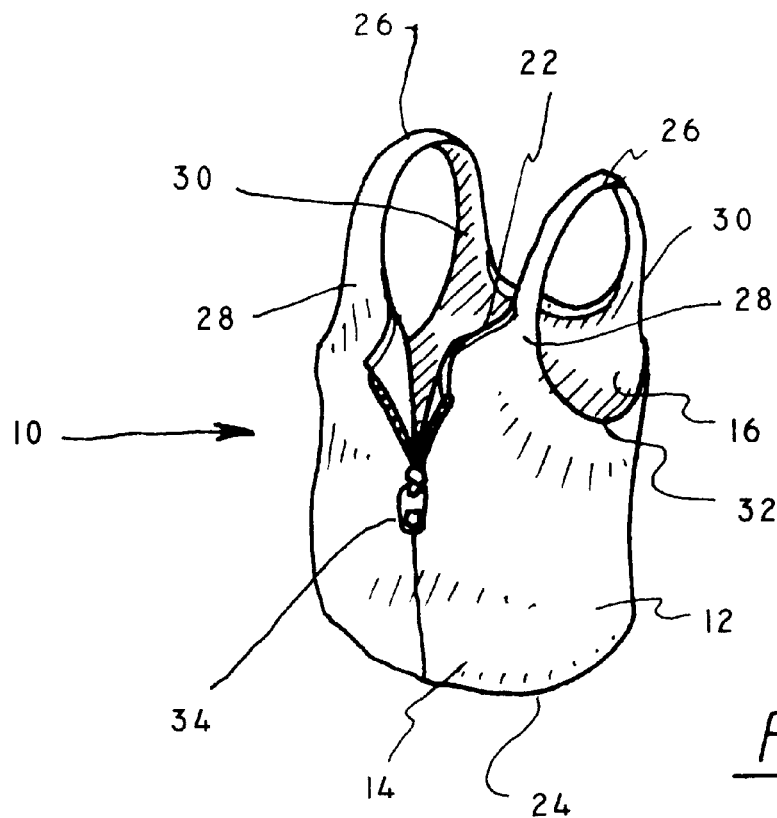
FIG. 1 is a schematic perspective view of a new protective torso garment according to the present invention.
Figure 2:
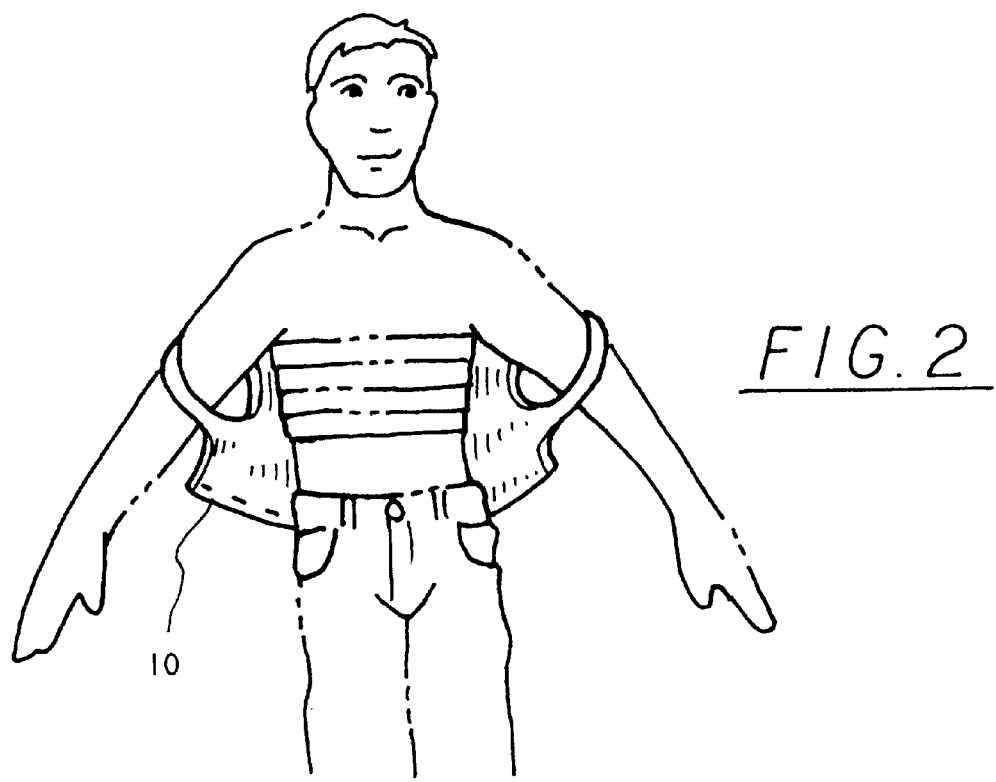
FIG. 2 is a schematic in-use view of the present invention.
Figure 3:
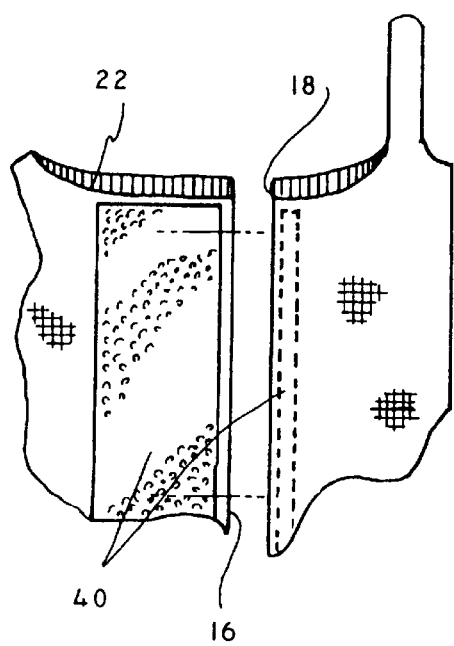
FIG. 3 is a schematic front view of the present invention.

With reference now to the drawings, and in particular to FIGS. 1 through 4 thereof, a new protective torso garment embodying the principles and concepts of the present invention and generally designated by the reference numeral 10 will be described.

As best illustrated in FIGS. 1 through 4, the protective torso garment 10 generally comprises a panel. The panel 12 has a outer surface 14, a inner surface 16, a first side edge 18, a second side edge 20, a top edge 22 and a bottom edge 24. The panel 12 comprises a conventional resiliently elastic cloth material.

Each of a pair of shoulder straps 26 has a first end 28 and a second end 30. Each of the ends 28, 30 the shoulder straps is securely attached to the top edge 22 of the panel 12. The second ends 30 are generally positioned between first 18 and second 20 side edges. Each of the first ends 28 of the straps is positioned respectively adjacent to one of the side edges 18, 20 of the panel 12. Portions 32 of the top edge 12 between adjacent ends 28, 30 of the straps 26 are downwardly arcuate for comfort, primarily in the armpit area.

Figure 4:
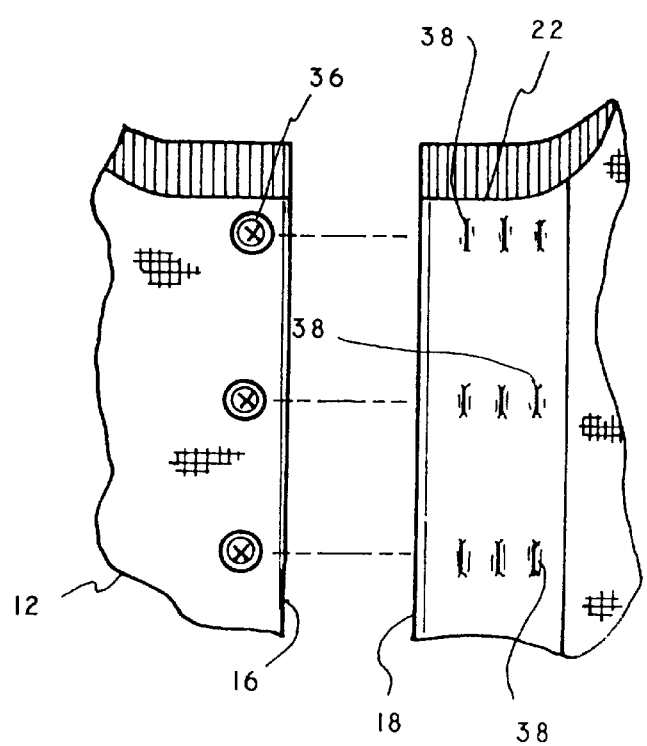
FIG. 4 is a schematic front view of the present invention.

A securing means detachably attaches the outer surface 14 of the panel 12 adjacent to first side edge 18 to the inner surface 16 of the panel 12 adjacent to the second side edge 20. The securing means may be a zipper 34, buttons 36 and corresponding apertures 38 or a hook and loop securing means 40. The hook and loop securing means 40 is the preferred means due to its sizing versatility. FIG. 4 shows the button 36 and corresponding aperture 38 embodiment. In that embodiment a plurality of buttons 36 is securely attached to the front surface 14 of the panel 12 and aligned generally adjacent to the first side edge 18. The panel 12 has a plurality of apertures 38 therein located generally adjacent to the second side edge 20. The apertures 38 are arranged in a matrix having a plurality of rows and columns. Each of the apertures 38 in a row is positioned to correspond with one of the buttons. The apertures 38 chosen will determine how tight the panel fits. Ideally, there are three columns of apertures.

In use, a person having a chest injury, such as broken rib, places their arms through the shoulder straps 26 and secures the first edge 18 to the second edge 20. The panel 12 is elastic to be tight and form fitting on the person. The panel 12 offers addition support to the person while being simple to put on and simple to remove.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A torso garment for protecting an injured ribcage, comprising:

a panel having an outer surface, an inner surface, a first side edge, a second side edge, a top edge and a bottom edge, said panel comprising a resiliently elastic material, such that said panel conforms to a form of a user whereby a garment size is adjustable;

a pair of shoulder straps, each of said shoulder straps having a first end and a second end, each of said ends of said shoulder straps being securely attached to said top edge of said panel, a neck opening being defined between said shoulder straps, said first and second side edges extending downwardly from said top edge to said bottom edge to form a front opening in said panel for facilitating putting said panel by a user over the injured ribcage and removal of said panel from over the injured ribcage; and a plurality of buttons mounted on said front surface of said panel adjacent to said first side edge and a plurality of apertures formed in said panel and located in a column generally adjacent to said second side edge for detachably attaching the first and second side edges with a selective degree of overlap of one of said side edges over the other of said side edges to permit adjustment of a perimeter size of said panel when secured by said buttons and apertures, said apertures being arranged in a matrix having a plurality of rows and columns, each of said apertures in a row being positioned to correspond with one of said buttons, the plurality of columns including columns positioned at a plurality of distances from said second side edge for providing a range of adjustment approximately equal to a distance between a column closest to said second side edge and a column farthest from said second side edge.

2. The torso garment for protecting an injured ribcage as in claim 1, wherein said plurality of columns is three columns.

* * * * *